Figure 1:
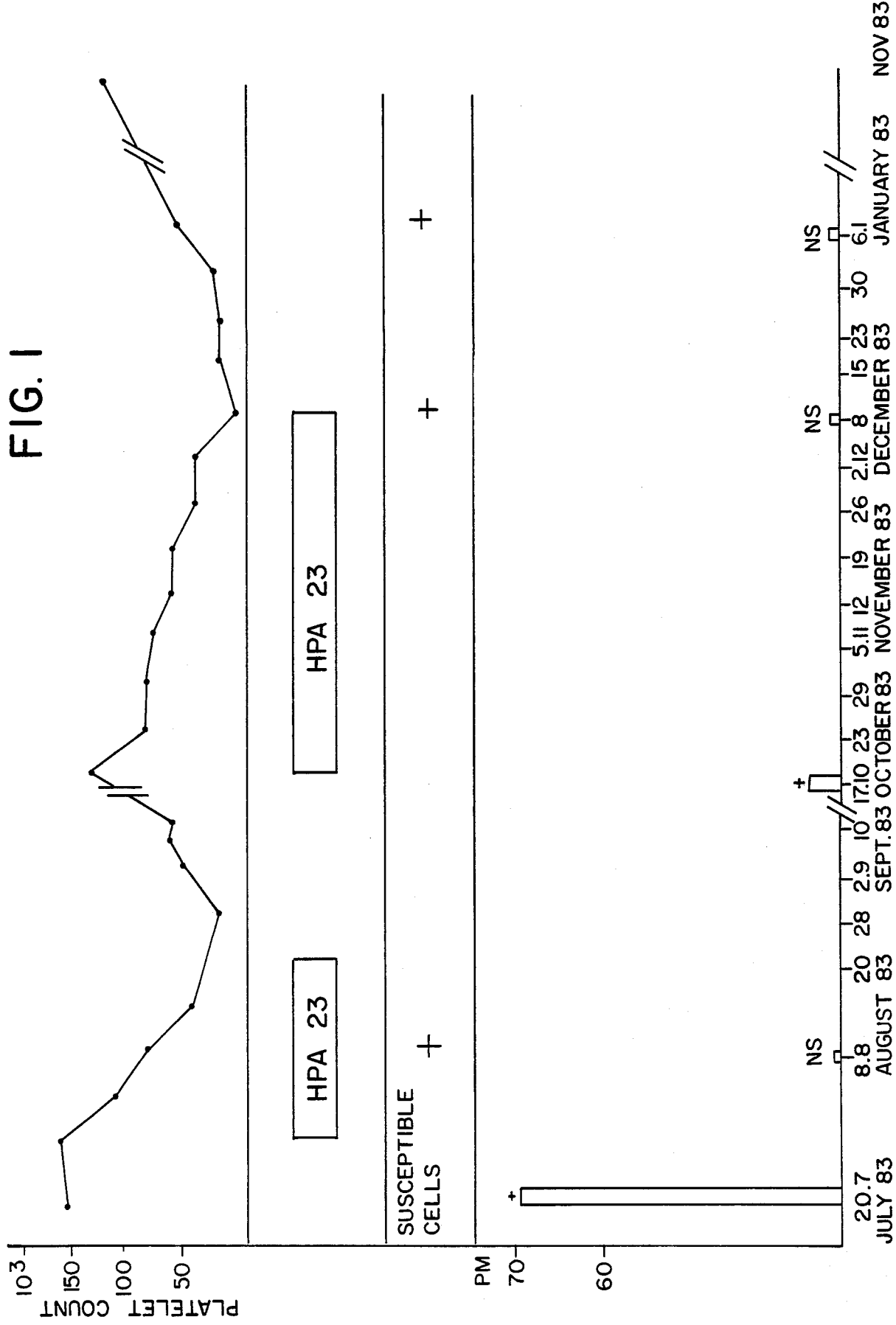

United States Patent [19]

Chermann et al.

[11] Patent Number: 4,759,929

[45] Date of Patent: * Jul. 26, 1988

[54] NOVEL TREATMENT

[75] Inventors: Jean-Claude Chermann, Elancourt; Dominique Dormont, La Celle St. Cloud; Etienne Vilmer, Sceaux; Bruno Spire, Garches; Francoise Barre-Sinoussi, Issy les Moulineaux; Luc Montagnier, Plessis-Robinson; Willy Rozenbaum, Paris, all of France

[73] Assignee: Cabinet Harle & Phelip, Paris, France

[*] Notice: The portion of the term of this patent subsequent to Oct. 15, 2002 has been disclaimed.

[21] Appl. No.: 11,156

[22] Filed: Feb. 5, 1987

Related U.S. Application Data

[63] Continuation of Ser. No. 678,240, Dec. 3, 1984, abandoned.

[51] Int. Cl.$^4$ ............................................. A61K 33/24
[52] U.S. Cl. ..................................................... 424/131
[58] Field of Search ......................................... 424/131

[56] References Cited

U.S. PATENT DOCUMENTS 4,547,369 10/1985 Chermann et al. ................. 424/131

Primary Examiner—Jerome D. Goldberg
Attorney, Agent, or Firm—Bierman and Muserlian

[57] ABSTRACT

A novel method of treating acquired immune deficiency syndromes in warm-blooded animals comprising administering to warm-blooded animals an amount of a non-toxic, pharmaceutically acceptable salt selected from the group consisting of alkali metal, alkaline earth metal and ammonium salts of 9-antimonio-III-21-tungsto-VI-sodate -III-21-tungsto-VI-sodate sufficient to combat acquired immune deficiency syndromes.

3 Claims, 2 Drawing Sheets

NOVEL TREATMENT

This is a continuation of Ser. No. 678,240 filed: Dec. 3, 1984, now abandoned.

STATE OF THE ART

Acquired immuno deficiency syndrome or AIDS is a condition characterized by serious opportunistic infections and/or Kaposi's sarcoma related to depressed cellular immunity and quantitative modification of T cell subpopulations. A syndrome of persistent generalized lymphadenopathy or PGL has been related to AIDS based on clinical and seroepidemiologic data. A human lymphocytophathic retrovirus, lymophoadenopathy associated virus or LAV identified in 1983, is considered to be the etiologic agent of AIDS. LAV and similar viruses named HTLV III by others, have been consistently isolated from patients with PGL or AIDS. The biochemical and biological properties of these two viruses are very similar and LAV RNA dependent DNA polymerase (Reverse Transcriptase: RT) characteristics have been published.

To date, no effective therapies for the underlying immune deficiency of AIDS and PGL have been developed despite limited effects of $\alpha$-interferon on Kaposi's sarcoma in some patients. To reduce or arrest the viral spread, one could imagine as therapeutic strategy the use of specific inhibitors on the viral enzyme required for replication. Among such compounds, ammonium 9-antimonio-III-21-tungsto-9-VI-sodate or HPA 23 was previously described as a competitive inhibitor of MLV reverse transcriptase. This drug is a cryptate mineral condensed ion, and has been shown to be active in vivo against a broad spectrum of RNA and DNA viruses. $HPA_{23}$ is also active in mice infected with slow viruses and it has been used previously in man to attempt treatment of Creutzfeldt-Jakob disease.

OBJECTS OF THE INVENTION

It is an object of the invention to provide a novel method of treating acquired immune deficiency syndromes in warm-blooded animals including humans.

This and other objects and advantages of the invention will become obvious from the following detailed description.

THE INVENTION

The novel method of the invention of treating acquired immune deficiency syndromes in warm-blooded animals comprises administering to warm-blooded animals an amount of a non-toxic, pharmaceutically acceptable salt selected from the group consisting of alkali metal, alkaline earth metal and ammonium salts of 9-antimonio-III-21-tungsto-VI-sodate sufficient to combat acquired immune deficiency syndromes. The preferred daily dosage is 0.1 to 100 mg/kg and the administration may be oral, parenteral or rectally.

Commonly assigned U.S. patent application Ser. No. 74,514 filed Sept. 11, 1979, now U.S. Pat. No. 4,547,369 which has an effective U.S. filing date of July 24, 1974 describes ammonium-21-tungsto-9-antimoniate (HPA 23) as a cryptate compound with a central cage in which metabolic ions can be located. HPA 23 and its other salts are active against a broad spectrum of RNA and DNA viruses in vivo and there is evidence that it can inhibit in vitro either viral or cellular polymerases. It protects in vivo against leukemia induced by Friend viruses and the plasma variant of Chirigos virus. HPA 23 also has some activity against lethal encephalomyocarditis infections of mice and it reduces the mortality of adult mice acutely infected by lymphatic choriomeningitis virus. It also reduces the occurance of spontaneous mammary tumors in $C_3HBi$ mice and can prevent disease or prolong the incubation period in mice infected with scrapie.

In the last decade, one of the most important developments in human carcinogenesis was the discovery of the T cell leukemia viruses ($HTLV_1$ and $HTLV_2$) and these members of the retroviruses family were also considered to be potential candidates for the cause of acquired immune deficiency syndrome (AIDS) since retroviruses were known to cause immunosuppression as well as tumors in many animal species, such as domestic cats.

Other human retroviruses, distinct from $HTLV_1$ and $HTLV_2$ have recently been isolated from patients with AIDS or AIDS related syndrome. The first one, lymphadenopathy associated virus (LAV) has been isolated from individuals with AIDS or with prodromal signs of AIDS. A second isolate, named $HTLV_3$ is strongly associated with AIDS and presents properties very similar to LAV. The implication of a retrovirus as the causative agent of AIDS is also supported by the discovery of a horizontally acquired retrovirus related to but distinct from the Mason Pfizer Monkey Virus (MPMV), as the cause of an AIDS like disease in monkeys called simian acquired immuno deficiency syndrome (SAIDS). AIDS in monkeys and man appears to be caused by retroviruses that are unique to each species, and the simian presents a resource for the development of experimental therapeutic trials.

HPA 23 and its related salts are active on RNA dependent DNA polymerases of two primate retroviruses thought to be involved in acquired immune deficiency syndromes (AIDS): Lymphadenopathy associated virus (LAV) in human and simian AIDS virus (SAIDS virus) in monkeys. Kinetic studies show a competitive inhibition of the viral enzyme by the product with both the human and monkey viruses. Competitive inhibition seems to be the general mechanism of reverse transcriptase inhibition of retroviruses by HPA 23.

In the following examples there are described several preferred embodiments to illustrate the invention. However, it should be understood that the invention is not intended to be limited to the specific embodiments.

EXAMPLE 1

Ammonium-9-antimonio-III-21-tungsto-VII-sodate or HPA 23 has the formula $17(NH_4)Na(NaSb_9W_{21}O_{86}).14H_2O$ and a molecular weight of 6800.

Simian AIDS (SAIDS) virus producing cells were provided by Murray Gardner, M.D. and supernatants of cell cultures were concentrated using polyethylene glycol (PEG) 10 percent precipitation. The precipitate was purified on a 20 to 60 percent sucrose gradient (50,000 g, 2.5 hours). Reverse transcriptase assays (see legend Table I) were performed on each fraction from the collected gradient. Maximum RT activity was found at a density of 1.18.

LAV Purification

Lymphadenopathy associated virus (LAV) was purified. Briefly, after clarification, the virus was concentrated by PEG (10 percent), and then centrifuged for 1.5 hours at 55,000 g (IEC type SB 498 rotor) on a 10 to 60 percent sucrose gradient. Reverse transcriptase assays were performed on each fraction and the maximum RT activity was found at a density of 1.16 and corresponded to the purified virus fraction.

LAV Reverse Transcriptase Purification

LAV RT was purified. Briefly, $10^9$ LAV infected cells were washed two times in PBS, resuspended in Tris 50 mM (pH 7.5) KCl 500 mM, ethylene diamine tetracetic acid (EDTA) 0.1 mM, dithiothreitol 1 mM and glycerol 10 percent, and frozen in liquid nitrogen. After incubation with Triton X100 0.01 percent at 37° C. (15 Min), cell homogenates were centrifuged at 100,000 g for one hour and the supernatant dialyzed six hours (KCl 100 mM). The dialyzate was chromatographed on a phosphocellulse column. RT and DNA polymerases were eluted from the column with a 0.1M to 1M KCl gradient.

Reverse Transcriptase Assays

Assay mixtures are indicated in the legend of Table I. The reaction was stopped by treating the mixtures with sodium pyrophosphate and trichloracetic acid. The results are given as picomoles of tritiated deoxyribonucleotides monophosphate incorporated into DNA after 1 hour at 37° C.

TABLE I

| Virus | Inhibitor μg/ml | p. mole incorporated | Percent inhibition | $ID_{50}$ μg/ml |
|---|---|---|---|---|
| SAIDS | 0 | 0.43 | 0 | 1.1 |
| virus | 0.5 | 0.34 | 21 | |
| | 1 | 0.28 | 35 | |
| | 2.5 | 0.09 | 80 | |
| | 5 | 0.024 | 94.5 | |
| | 10 | 0.0025 | 99.5 | |
| | 25 | 0 | 100 | |
| LAV | 0 | 0.13 | 0 | 30.5 |
| virus | 10 | 0.127 | 2.4 | |
| | 25 | 0.013 | 18.6 | |
| | 50 | 0.098 | 84.4 | |
| | 60 | 0 | 100 | |
| LAV | 0 | 0.11 | 0 | 11 |
| purified | 0.5 | 0.105 | 4.5 | |
| RT | 1 | 0.101 | 8.2 | |
| | 5 | 0.073 | 33.6 | |
| | 10 | 0.062 | 43.6 | |
| | 20 | 0.042 | 61.8 | |
| | 30 | 0.032 | 70.2 | |
| | 60 | 0.007 | 94 | |
| | 100 | 0 | 100 | |

HPA 23 inhibition of reverse transcriptase of SAIDS virus and LAV. Reaction mixture (50 μl) contains: Tris 50 mM pH 7.9, 5 mM MgCl$_2$, 20 mMKCl, 2 mM dithiothreitol, 0.01% Triton X100, 0.05 OD/ml polyA, 0.05 OD/ml Oligo dT 12–18, and 200 pM$^3$HTTP (25 Ci/mM).

RESULTS

1. Inhibition of Simian AIDS Virus Reverse Transcriptase by $HPA_{23}$

The results of Table I show that SAIDS virus reverse transcriptase is strongly inhibited as a function of the dose of $HPA_{23}$. The concentration of $HPA_{23}$ giving a 50 percent inhibition of this reaction ($ID_{50}$) is 1.1 μg/ml.

2. Inhibition of LAV Reverse Transcriptase by $HPA_{23}$

The results of Table I show LAV reverse transcriptase is also inhibited by $HPA_{23}$ but required doses are higher than in SAIDS model: $ID_{50}$ is 30 μg/ml.

3. Inhibition of LAV Purified Reverse Transcriptase by $HPA_{23}$

The results of Table I further show that purified RT is also inhibited by $HPA_{23}$, but the $ID_{50}$ (11 μg/ml) is lower than that required for the inhibition of the LAV non purified RT, possibly due to a better contact between the enzyme and the compound.

4. Effect of Synthetic Template Primer Concentration on the $HPA_{23}$ Inhibition of LAV Purified Reverse Transcriptase The results of the Lineweaver-Burk plots of the effects of varying concentration of poly An oligo dT12–18 at two different $HPA_{23}$ concentrations are summarized in FIG. 1. In the experimental conditions, kinetic enzymatic parameters are: $KM = 2.18$ nM of polyA oligo dT, $V_{max} = 0.02$ pM of 3 HTMP incorporated sec$^{-1}$. This figure illustrates the competitive inhibition mechanism of $HPA_{23}$, as described previously with Murine Leukemia Virus (MLV) reverse transcriptase inhibition by $HPA_{23}$. The interaction of $HPA_{23}$ with the template primer-enzyme complex should take place at the binding site of the template primer.

$HPA_{23}$ is an inhibitor of reverse transcriptase of both LAV and SAIDS retrovirus and these results are confirmed by the compounds action on numerous animal retorviruses including Murine Leukemia Virus. Unpublished results showed that this compound does not inhibit pancreatic DNase and RNase, and *E. Coli* RNase H; on the other hand, $HPA_{23}$, is also known to be a strong inhibitor of *E. Coli* DNA and RNA polymerases, and of mammalian cellular DNA polymerases. $HPA_{23}$ has also been found to be an inhibitor of mouse α DNA polymerase without any effect on β DNA polymerase. In this model, the required doses are much higher than those inhibiting reverse transcriptase. Also, because the α polymerase is the cell cycle DNA polymerase, one can see that the dose required to inhibit the cell growth is twenty times higher than the one blocking RT activity. Then, in vivo, using a mouse model, the inhibition of the viral replication occurs without cellulose.

The mechanism of the RT inhibition is identical to the one shown in other retroviral models. Therefore competitive inhibition appears to be the general mechanism of action of $HPA_{23}$ on reverse transcriptase, even if required doses are different in human and animal models. $HPA_{23}$ was also found to be neurotropic and to be a stimulating agent of natural killer (NK) and killer cells (ADCC) function. This suggests that the in vivo activity of this compound on retrovirus infections may be explained by effects both on the immune system and on viral replication. The simian AIDS could be used as a model for testing the action of antiviral drugs despite differences in clinical and immunologic patterns of AIDS and SAIDS.

Numerous therapies have been proposed to treat AIDS patients but, no evidence of successful therapy has been reported in spite of limited effects on either biological or clinical parameters. As mentioned above, $HPA_{23}$ is acting on the immune system as well as specifically on the enzyme required for virus replication (RT); moreover serologic studies have demonstrated that a high percentage of anti LAV antibodies could be detected in AIDS related complex (ARC) and AIDS patients.

Lineweaver-Burk representation of the influence of poly A oligo $T_{12-18}$ template concentration on the inhibition by $HPA_{23}$ of LAV purified reverse transcriptase
A: picomoles of $^3$H TMP incorporated in five minutes at 37° C.
B: template primer concentration (OD ml$^{-1}$)

—: control (no inhibition)
■-■: inhibition dose corresponds to 65 percent HPA$_{23}$ inhibition (19 μg/ml)
●-●inhibition dose corresponds to 80 percent HPA$_{23}$ inhibition (40 μg/ml)
Each plot-point is the mean of three experiments.

EXAMPLE 2

Four patients with AIDS or related syndrome were selected by the isolation of LAV by culture of peripheral blood cells and LAV was detected in cell-free supernatants by its reverse transcriptase activity. The description of clinical features is summarized in Table II.

The first patient received two courses of HPA$_{23}$ using I.V bolus infusion (about two minutes). The treatment schedule and dosage are described in FIG. 2 and its legend. Pharmacokinetic studies showed a fast elimination (half life shorter than 20 minutes). Therefore the drug was given by slow IV infusion to the other patients. Patients 2, 3 and 4 received 200 mg of HPA$_{23}$ by IV infusion in 250 ml of isotonic glucose for 3 hours per day during 15 days.

All criteria for a new drug in humans including informed consent were used and the following parameters were determined twice a week: blood, liver and kidney biochemical and biological parameters, and according to previous assay in Creutzfeldt-Jakob disease, each patient was under electroencephalogramm (EEG) recording.

Viral production assays were performed before, during and after the HPA$_{23}$ treatment as described in legend of figures two and three. T cell lymphocytes cultures and cocultures were performed as previously described. Briefly, T lymphocyte were cultured in RPMI 1640 medium supplemented with 10% FCS, TCGF, antihuman α interferon serum, polybrene and antibiotics. Virus production was followed in cell free supernatant by measuring the RT activity twice a week. RT assays were conducted as published earlier. For each assay, fractionnated T lymphocytes were cultivated or cocultivated for virus isolation or infected with its own previous virus isolated for detection or viral susceptible cells.

RESULTS

1. Effect of HPA$_{23}$ Therapy on the Isolation of LAV from Peripheral Blood Specimens (in Vivo Replication)

a—Patient 1

During each period of treatment, LAV could no longer be detected in T cell cultures, but between the two courses of treatment, virus was again detectable. The treatment was discontinued after a total of two courses. At the end of the treatment, LAV was not detectable and infection of his own T lymphocytes by the virus isolated of this patient was possible, showing the presence of LAV target cells. These results are summarized in FIG. 2.

b—Patients 2, 3 and 4

In all patients, LAV was isolated immediately prior to therapy. Following two weeks treatment with HPA$_{23}$, no virus (LAV) was isolated from both primary cultures of patients T cells and cocultures of patient T cells with T cells from healthy donors. (FIG. 3). Both cultures and cocultures were observed for one month; 30 days after the end of the treatment, LAV was again detected in the T cell cocultures in two of the three patients (3 and 4) at a very low level, and in the 4 cases some susceptible cells were detected as shown in FIG. 3.

2. Effect of HPA$_{23}$ on T$_4$+ Lymphocytes Number

The absolute numbers of T$_4$+ cells and T$_4$/T$_8$ ratio did not change significantly after therapy.

3. Toxicity

HPA$_{23}$ therapy was associated with some platelet toxicity in three out of four cases. As early as day 8, the platelet numbers typically decreased in 2 of the 4 patients and further slight decrease continued until the end of the HPA$_{23}$ course. Recovery of the platelet count to the pretreatment value in each adult patient was observed between 21st day and the 45th day after. Mild elecoations of the hepatic transaminases (2×normal value) were observed in patients 2, 3 and 4 during treatment. Recovery of the pretreatment range occured within 21 days. No new renal toxicity was observed.

DISCUSSION

HPA$_{23}$ is able to inhibit LAV replication in four patients with AIDS or related syndrome, treated with this product. The results show first the LAV is no more

TABLE II

| | | | | | | Abs. T$_4$+ | | | | |
|---|---|---|---|---|---|---|---|---|---|---|
| Patient | Sex | Age | Group risk | Date of the Diagnosis | Clin. manifes. | cell number | Date of LAV isolat. | LAV antibodies (*) | Date of HPA 23 Treatment | Current status |
| 1 | M | 13 | Hemoph. | May 83 | Brain TX | 9 | May 83 | + | July 26$^{th}$ 83 | Alived |
| 2 | F | 30 | Haiti | May 84 | PCP | 32 | May 84 | + | July 7$^{th}$ 84 | Alived |
| 3 | M | 30 | HS, USA | April 84 | PCP KS | 141 | May 84 | + | June 11$^{th}$ 84 | Alived |
| 4 | M | 30 | Haiti | April 84 | PGL Oral thrush | 1.70 | May 84 | + | June 17$^{th}$ 84 | Alived |

CLINICAL PRETREATMENT STATUS OF THE PATIENTS

TX: Toxoplasmosis
PCP: *pneumocystis carinii pneumoniae*
PGL: persistent generalized lymphadenopathy
KS: Kaposi's *sarcoma*
hemoph: hemophiliac
HS: Homosexual
M: Male. F: Female
(*) + means ELISA and RIPA ($^{35}$S methionine)

isolated from peripheral T lymphocytes during or after treatment, second that their own cells could be reinforced by their own viruses, demonstrating that susceptible cells are present. One month after treatment, LAV was recovered from two AIDS patients either from stimulated lymphocytes or by cocultivation technics. Moreover, when no virus was found, an assay of infection of these cells by LAV was performed, showing that the compound was inhibiting the replication of the virus and was not killing the viral infected cells. This fact is in agreement with the previously observed in vitro R.T. competitive inhibition of retroviruses by $HPA_{23}$. Doses required to inhibit reverse transcriptases are lower than those inhibiting cellular DNA polymerases and, therefore, viral replication inhibition occurs without cellulose cytotoxicity.

In two of the four patients (patients 1 and 2), LAV was not isolated one month after the end of the treatment, even after cocultivation, indicating that the viral amount in the cells was below detecting methods. In the two other patients LAV was again detectable only by cocultivation, indicating an incomplete inhibition; this incomplete inhibition of LAV replication could be also explained because $HPA_{23}$ cannot reach all infected targets.

LAV is the cause of AIDS but an antiretroviral drug such as $HPA_{23}$ may not be sufficient to cure AIDS because (1)—LAV could have done all its cytopathogenic effect on some precursor cells at the time of the treatment. (2)—inhibition of LAV replication is not sufficient to completely restore the diffuse immunologic dysfunction. (3)—autoimmune mechanisms may be involved in AIDS pathogenesis.

These theoretical questions are difficult to answer and a rational use of antiviral drugs could help to solve this problem.

Prognosis or natural history of AIDS is not easy to determine. However, after $HPA_{23}$ treatment, some clinical features are noted: patient one, one year after the end of $HPA_{23}$ therapy, did not present anymore other opportunistic infections, despite persistance of a low absolute number of $T_4+$ cells. Parallely with the incomplete LAV inhibition, patient 3 stabilized his mucosal evolutive K.S., without regression (4 months outcome). The condition of the two other patients improved but, because of their clinical status, the observation time is too short to relate improvement and $HPA_{23}$ therapy.

Various modifications of the method may be made without departing from the spirit or scope thereof and it is to be understood that the invention is intended to be limited only as defined in the appended claims.

LEGEND OF FIG. 2

Figure 2:
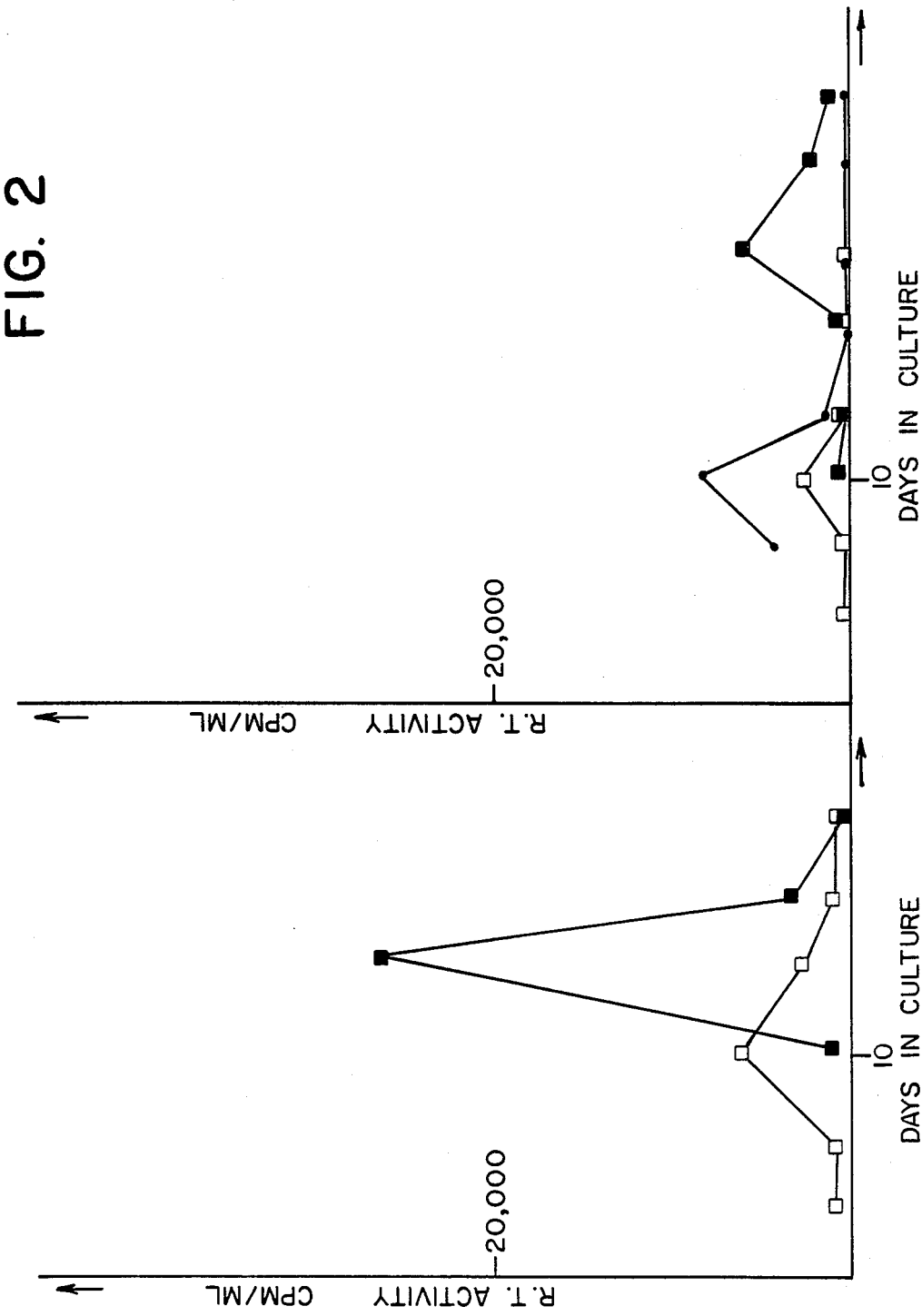

FIG. 2 summarized LAV replication tested by Reverse transcriptase activity in supernatants of T cell cultures and platelets count pattern during $HPA_{23}$ treatment of patient 1. This patient received two periods of treatment: first period from July 27th to Aug. 20th 1983. Cumulative doses were respectively 890 mg and 1980 mg. In each period, $HPA_{23}$ doses were slight increased from 1 mg/kg to 3.3 mg/kg.

LEGEND OF FIG. 3

Reverse transcriptase pattern before (left) and after (right) $HPA_{23}$ treatment in Patient 2.
□ Patient T cells culture
■ Coculture wet
● Reinfection assay

What is claimed is:

1. A method of treating acquired immune deficiency syndromes in warm-blooded animals comprising administering to warm-blooded animals an amount of a non-toxic, pharmaceutically acceptable salt selected from the group consisting of alkali metal, alkaline earth metal and ammonium salts of 9-antimonio-III-21-tungsto-VI-sodate sufficient to combat acquired immune deficiency syndromes.

2. The method of claim 1 wherein the salt administered is the ammonium salt.

3. The method of claim 2 wherein the salt is administered parenterally.

* * * * *

UNITED STATES PATENT AND TRADEMARK OFFICE
CERTIFICATE OF CORRECTION

PATENT NO. : 4,759,929
DATED : July 26, 1988
INVENTOR(S) : JEAN-CLAUDE CHERMANN et al It is certified that error appears in the above-identified patent and that said Letters Patent is hereby corrected as shown below:

| Col. | Line | |
|------|------|---|
| | | Assignee, title page |
| [73] | | "Cabinet Harle & Phelip" should be --Institut Pasteur, Paris, France-- |
| 2 | 51&52 | "17($NH_4$)Na($NaSb_9W_{21}O_{86}$)" should be --17($NH_4$)Na($NaSb_9W_{21}O_{86}$)-- |

Signed and Sealed this

Tenth Day of January, 1989

Attest:

DONALD J. QUIGG

Attesting Officer          Commissioner of Patents and Trademarks